(12) United States Patent
McQueston et al.

(10) Patent No.: US 9,245,374 B2
(45) Date of Patent: Jan. 26, 2016

(54) SPACE CARVING IN 3D DATA ACQUISITION

(75) Inventors: James H. McQueston, Winchester, MA (US); Ilya A. Kriveshko, Littleton, MA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 274 days.

(21) Appl. No.: 14/000,446

(22) PCT Filed: Feb. 17, 2012

(86) PCT No.: PCT/US2012/025548
§ 371 (c)(1),
(2), (4) Date: Aug. 20, 2013

(87) PCT Pub. No.: WO2012/115862
PCT Pub. Date: Aug. 30, 2012

(65) Prior Publication Data
US 2013/0335417 A1    Dec. 19, 2013

Related U.S. Application Data

(60) Provisional application No. 61/445,499, filed on Feb. 22, 2011.

(51) Int. Cl.
*G06T 15/08* (2011.01)
*A61B 6/14* (2006.01)
*A61B 6/00* (2006.01)
*A61C 19/04* (2006.01)

(52) U.S. Cl.
CPC ............. *G06T 15/08* (2013.01); *A61B 6/145* (2013.01); *A61B 6/5205* (2013.01); *A61B 6/466* (2013.01); *A61C 19/04* (2013.01)

(58) Field of Classification Search
None
See application file for complete search history.

(56) References Cited

U.S. PATENT DOCUMENTS

| 5,410,614 | A | 4/1995 | Chou |
| 7,372,642 | B2 | 5/2008 | Rohaly |
| 2003/0151604 | A1 | 8/2003 | Kaufman |
| 2004/0125103 | A1* | 7/2004 | Kaufman et al. ............. 345/419 |
| 2004/0155975 | A1 | 8/2004 | Hart |
| 2006/0139470 | A1 | 6/2006 | McGowan |
| 2007/0103460 | A1 | 5/2007 | Zhang |
| 2007/0171220 | A1 | 7/2007 | Kriveshko |
| 2007/0172101 | A1 | 7/2007 | Kriveshko |

(Continued)

FOREIGN PATENT DOCUMENTS

| WO | WO 2007-084589 | 7/2007 |
| WO | WO 2012-115863 | 8/2012 |

OTHER PUBLICATIONS

J. Morita Mfg. Corp., "3D Accuitomo 170," 2009.*

(Continued)

*Primary Examiner* — Kee M Tung
*Assistant Examiner* — Nicholas R. Wilson

(57) ABSTRACT

Three-dimensional scanning is improved with the use of space carving to exclude certain scan results from processing and display. Using space carving techniques, a spatial matrix is maintained to store data on volumetric regions (or voxels) known to be empty. By excluding or modifying processing of outlier data from within these unoccupied voxels, a three-dimensional reconstruction process can achieve concurrent improvements in accuracy and speed. In addition, a real time display of scan results can be improved by modifying how such outliers are rendered.

26 Claims, 6 Drawing Sheets

(56) References Cited

U.S. PATENT DOCUMENTS

| | | | |
|---|---|---|---|
| 2009/0232353 A1* | 9/2009 | Sundaresan et al. | 382/103 |
| 2010/0066364 A1 | 3/2010 | Huwer | |
| 2010/0281370 A1 | 11/2010 | Rohaly | |
| 2010/0303341 A1 | 12/2010 | Hausler | |

OTHER PUBLICATIONS

Kutulakos et al., "A Theory of Shape by Space Carving," International Journal of Computer Vision, 2000.*

Snow et al., "Exact Voxel Occupancy with Graph Cuts," IEEE, 2000.*

Curless et al., "A Volumetric Method for Building Complex Models from Range Images," ACM, 1996.*

Lorensen et al., "Marching Cubes: A High Resolution 3D Surface Construction Algorithm," ACM, 1987.*

Benjemaa, "A Solution for the Registration of Multiple 3D Point Sets Using Unit Quaternions", Proc. ECCV, Jun. 1998, pp. 34-50.

Dorst, "First Order Error Propagation of the Procrustes Method for 3D Attitude Estimation", IEEE Transactions on Pattern Analysis and Machine Intelligence, Feb. 2005, vol. 27, No. 2, pp. 221-229.

Govindu "Combining Two-View Constraints for Motion Estimation," Proc. of the Int. Conf. on Computer Vision and Pattern Recognition, Jul. 2001, vol. 2, pp. 218-225.

Krishnan, "Global Registration of Multiple 3D Point Sets via Optimization-on-a-Manifold," Eurographics Symposium on. Geometry Processing, 2005, 11 pages.

Williams, "Simultaneous Registration of Multiple Corresponding Point Sets", Computer Vision and Image Understanding, Jan. 2001, vol. 81, No. 1, pp. 117-142.

International Search Report for International PCT Application No. PCT/US2012/025548, Mailed on Aug. 22, 2012, 3 pages.

* cited by examiner

SPACE CARVING IN 3D DATA ACQUISITION

BACKGROUND

1. Field of the Invention

The invention relates to the use of space carving to improve three-dimensional data acquisition.

2. Description of the Related Art

A wide range of techniques exist for acquiring three-dimensional data from a subject. One broad category of techniques employs continuous scanning in which incremental three-dimensional data is acquired and assembled into a full three-dimensional model. In this latter category, regardless of the particular scanning technology, the calculation and display of three-dimensional data can become encumbered by transient obstructions within a scanning volume. For example, in a dental scan, a patient's tongue or other soft tissue may temporarily obstruct or move adjacent to a scanned surface. A technician may similarly obstruct a scanner's view of the scanned surface with a finger, tongue depressor, or other instrument. There remains a need for techniques to exclude such outliers from a three-dimensional scanning process.

SUMMARY

Three-dimensional scanning is improved with the use of space carving to exclude certain scan results from processing and display. Using space carving techniques, a spatial matrix is maintained to store data on volumetric regions (or voxels) known to be empty. By excluding or modifying processing of subsequent outlier data from within these unoccupied voxels, a three-dimensional reconstruction process can achieve concurrent improvements in accuracy and speed. In addition, a real time display of scan results can be improved by modifying how such outliers are rendered.

In one aspect, a method disclosed herein includes storing a spatial matrix in a memory, the spatial matrix including information for a plurality of voxels in a mesh of a scan space; obtaining three-dimensional data from an object within the scan space using a scanner; identifying a one of the plurality of voxels in the mesh that is unoccupied; storing an indication in the spatial matrix for a modified processing of data from the one of the plurality of voxels, thereby identifying a prohibited volume within the scan space; and processing a portion of the three-dimensional data that is not in the prohibited volume according to an unmodified processing and processing a second portion of the three-dimensional data that is in the prohibited volume according to the modified processing.

Identifying the one of the plurality of voxels may include identifying a plurality of points on a ray between the scanner and the object that are unoccupied. The method may include providing a spatial margin of one or more voxels adjacent to a surface of the object for which processing cannot be prohibited. The spatial margin may be a multiple of a standard deviation of a z-axis measurement for the scanner. The modified processing may include detecting a point in the prohibited volume and displaying the point with a decay time. The modified processing may include omitting any points in the prohibited volume from a surface mesh of the object created with the three-dimensional data. The mesh may divide the scan space into a spatial grid substantially identical to a second spatial grid used to create the surface mesh. The modified processing may include omitting any points in the prohibited volume from a high-accuracy refinement of the three-dimensional data. The mesh of the scan space may be subdivided into voxels having a substantially cubic shape. The substantially cubic shape may measure about 250 microns on each edge. The prohibited volume may include more than one of the plurality of voxels. The spatial matrix may include a binary flag for each one of the plurality of voxels that indicates whether processing is permitted or forbidden for a corresponding volume of the scan space.

In another aspect, a computer program product disclosed herein includes computer executable code embodied on a non-transitory computer readable medium that, when executing on one or more computing devices, performs the steps of: storing a spatial matrix in a memory, the spatial matrix storing information for a plurality of voxels in a mesh of a scan space; obtaining three-dimensional data from an object within the scan space using a scanner; identifying one of the plurality of voxels in the mesh of the scan space that is unoccupied; storing an indication in the spatial matrix for a modified processing of data from the one of the plurality of voxels that contains the point, thereby identifying a prohibited volume within the scan space; and processing a portion of the three-dimensional data in the prohibited volume according to the modified processing and processing a second portion of the three-dimensional data that is not in the prohibited volume according to an unmodified processing.

In another aspect, a system disclosed herein includes a scanner configured to obtain three-dimensional data from an object within a scan space; a memory configured to store a spatial matrix that includes information for a plurality of voxels in a mesh of a scan space; and a processor configured to identify a point in the scan space that is unoccupied, to store an indication in the spatial matrix for a modified processing of data from a one of the plurality of voxels that contains the point, thereby identifying a prohibited volume within the scan space, to process a portion of the three-dimensional data that is not in the prohibited volume according to an unmodified processing, and to process a second portion of the three-dimensional data that is in the prohibited volume according to the modified processing.

In another aspect, a system disclosed herein includes storing means for storing a spatial matrix that includes information for a plurality of voxels in a mesh of a scan space; scanning means for obtaining three-dimensional data from an object within the scan space; and processing means for identifying a point in the scan space that is unoccupied, storing an indication in storing means for a modified processing of data from a one of the plurality of voxels that contains the point, thereby identifying a prohibited volume within the scan space, processing a portion of the three-dimensional data that is not in the prohibited volume according to an unmodified processing and processing a second portion of the three-dimensional data that is in the prohibited volume according to the modified processing.

BRIEF DESCRIPTION OF THE FIGURES

The invention and the following detailed description of certain embodiments thereof may be understood by reference to the following figures.

DETAILED DESCRIPTION

Figure 1:
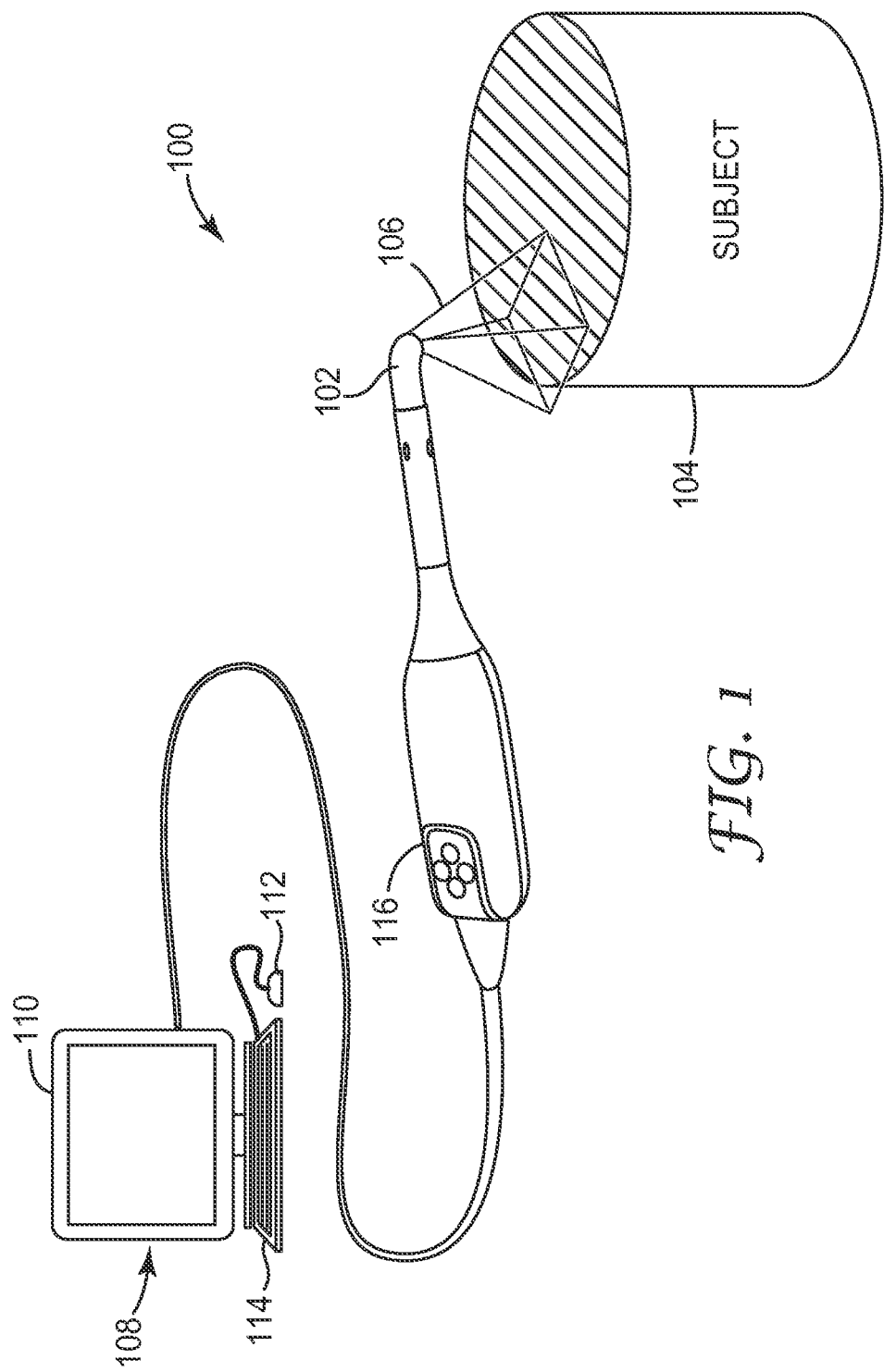
FIG. 1 shows a dental image capture system.

The following description relates to use of space carving techniques to improve processing of three-dimensional data acquired from a three-dimensional scanner. While the description emphasizes continuous scanning and dental applications, it will be appreciated that the inventive concepts disclosed herein are not limited to the specific embodiments disclosed. For example, the space carving techniques described herein may be used to improve any three-dimensional acquisition or processing in which the capture of three-dimensional data occurs over a period of time such as structured light projection, x-ray computed tomography, optical coherence tomography, interferometry, and the like. The techniques described herein may similarly be employed in any three-dimensional processing environment where accuracy or time of computation can benefit from the exclusion of outlier data. Similarly, while the following description emphasis use of space carving to avoid processing known outliers, the approach may be readily generalized by, for example, by identifying multiple objects in a scan volume and excluding objects that are not rigidly associated with a scan subject. All such variations that would be apparent to one of ordinary skill in the art are intended to fall within the scope of this disclosure.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject, such as might be reconstructed from a number of two-dimensional views. In a three-dimensional image capture system, a number of such point clouds may also be registered and combined into an aggregate point cloud constructed from images captured by, for example, a moving camera. Thus it will be understood that pixels generally refer to two-dimensional data and points generally refer to three-dimensional data, unless another meaning is specifically indicated or otherwise clear from the context.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, a particle system, or any other renderable primitives or other data representing all or some of the surface of an object, as might be obtained through the capture and/or processing of three-dimensional scan data, unless a different meaning is explicitly provided or otherwise clear from the context.

A "three-dimensional representation" may include any of the three-dimensional surface representations described above, as well as volumetric, vector, and/or other representations, unless a different meaning is explicitly provided or otherwise clear from the context.

In general, the terms "render" or "rendering" refer to a two-dimensional visualization of a three-dimensional object, such as for display on a monitor. However, it will be understood that stereoscopic, three-dimensional, and other rendering technologies exist, and may be usefully employed with the systems and methods disclosed herein to render objects in three dimensions. As such, rendering should be interpreted broadly unless a narrower meaning is explicitly provided or otherwise clear from the context.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in various types of occlusion, soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture which may not be intraoral structures as described above, such as dental models (full and/or partial), wax-ups, investment molds, and the like, as well as trays, bases, dies, and other components employed in the fabrication of restorations, prostheses, and the like. Dental objects may be categorized in a number of ways. For example, dental objects may be categorized as natural dental objects such as the teeth, bone, and other intraoral structures described above and artificial dental objects such as the restorations, prostheses, appliances, hardware, and interim components of dental manufacture as described above. Similarly, dental objects may be categorized intraoral dental objects (which may be natural or artificial) and extraoral dental objects (which are generally but not exclusively artificial).

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified or otherwise clear from the context, the term "model", when used alone, may refer to either or both of a physical model and a digital model.

FIG. 1 shows an image capture system. In general, the system 100 may include a scanner 102 that captures images of a subject 104 within an image plane 106, and forwards the images to a computer 108, which may include a display 110 and one or more user input devices such as a mouse 112 or a keyboard 114.

The scanner 102 may include any camera or camera system suitable for capturing images from which a three-dimensional point cloud may be recovered. For example, the scanner 102 may employ a multi-aperture system as disclosed, for example, in U.S. Pat. Pub. No. 20040155975 to Hart et al. While Hart discloses one multi-aperture system, it will be appreciated that any multi-aperture system suitable for reconstructing a three-dimensional point cloud from a number of two-dimensional images may similarly be employed, including systems with moving apertures, fixed apertures, and/or electro-mechanically shuttered apertures. In one multi-aperture embodiment, the scanner 102 may include a plurality of apertures including a center aperture positioned along a center optical axis of a lens and any associated imaging hardware. The scanner 102 may also, or instead, include a stereoscopic, triscopic or other multi-camera or other configuration in which a number of cameras or optical paths are maintained in fixed or moving relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging (for example, time of flight in a known direction), or any other technology suitable for acquiring three-dimensional data, or two-dimensional data that can be resolved into three-dimensional data.

In one embodiment, the scanner 102 is a handheld, freely positionable probe having at least one user input device, such as a button, lever, dial, thumb wheel, switch, or the like, for user control of the image capture system 100 such as starting and stopping scans. In an embodiment, the scanner 102 may be shaped and sized for dental scanning. More particularly, the scanner may be shaped and sized for intraoral scanning and data capture, such as by insertion into a mouth of an imaging subject and passing the imaging plane 106 over one or more intraoral structures at a suitable distance to acquire surface data from teeth, gums, and so forth. The scanner 102 may, through such a continuous acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition. In other structured light systems, the illumination may be in the form of an array of laser beams that form a pattern on a surface, which pattern may be employed to recover three-dimensional data from the surface. Other systems employ a single laser beam along with directional information to gather point-by-point direction and range information. All such imaging systems may be usefully employed to acquire three-dimensional data as described herein.

The subject 104 may be any object, collection of objects, portion of an object, or other subject matter. While illustrated in FIG. 1 as a simple geometric form, the subject 104 may include much more complex surfaces, and any number of separate elements. For example, in a dental imaging application, the subject 104 may include a tooth, a quadrant of teeth, or a full collection of teeth including two opposing arches from which a virtual dental impression is desired. The subject 104 may also, or instead, include a dental prosthesis such as an inlay, a crown, or any other dental prosthesis, implant, or the like. The subject 104 may include a dental model, such as a plaster cast, wax-up, impression, or negative impression of a tooth, teeth, soft tissue, or some combination of these. An optical or textured imaging agent may optionally be applied to surfaces of the subject 104 to improve capture of three dimensional points. In other embodiments, the subject 104 may be a human head, or a portion thereof, from which a three-dimensional model may be acquired for custom fitting of a hearing aid, eyeglasses, goggles, or the like. In other embodiments, the subject 104 may be a physical model of an object for use in digital animation, such as a miniature, physical model for use in a three-dimensional digital animation process. From the preceding examples, it will be apparent that a system using the techniques described herein may be suitably adapted to a wide range of applications for relatively short range, high resolution three-dimensional image acquisition. However, one skilled in the art will appreciate that suitable adaptations to the image capture system 100 may be made for a variety of other three-dimensional imaging applications based upon multi-aperture or multi-camera systems, as well as other three-dimensional imaging systems and technologies, and all such variations are intended to fall within the scope of this disclosure.

The image plane 106 may include a two-dimensional field of view of the scanner 102. It will be appreciated that the term "image plane" as used in this paragraph, refers to a plane in the imaging environment rather than a plane within an optical sensor (such as film or sensors) where an image is captured. Though illustrated as a rectangle the image plane 106 may, for example, form a square, a circle, or any other geometry provided by the scanner 102. In general, the scanner 102 will have a depth of field or range of depth resolution that, together with the field of view 106, specifies a measurement volume of the scanner 102. The depth of field may vary with environmental conditions such as lighting (ambient or artificial), the texture or optical properties of the imaging subject, and so forth. It will further be understood that the term "field of view", as used herein may refer to a two-dimensional field such as an internal plane within the optics of an imaging system, an external plane such as a field in an imaging environment, or a region in a display, or may refer to a three-dimensional region such as a current measurement volume in an imaging environment. Thus, "field of view" as used herein should be interpreted in the broadest sense possible, unless a more specific meaning is explicitly provided, or otherwise clear from the context.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies, but may generally be considered to fall between about ten frames per second and about thirty frames per second for many of the applications described herein. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, for example, a radio frequency, infrared, ultrasound or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. One useful example of such a technique is described in commonly-owned U.S. application Ser. No. 11/270,135, filed on Nov. 9, 200. However, it will be appreciated that this example is not limiting, and that the principles described herein may be applied to a wide range of three-dimensional image capture systems. It will also be understood that terms such as "video" or "video rate" imply a wide range of possible frame rates associated with such video. While most modern video formats employ a frame rate of 25 to 30 frames per second, early video employed frame rates as low as 8 frames per second, and movies of the early 1900's varied from 12 to 18 frames per second. In addition, it is common for specialized imaging equipment to employ a rate adapted to the computational demands of particular imaging and rendering techniques, and some video systems operate with frame rates anywhere from 4 frames per second (for computationally extensive imaging systems) to 100 frames per second or higher (for high-speed video systems). As used herein, the terms video rate and frame rate should be interpreted broadly. Notwithstanding this broad meaning, it is noted that useful and visually pleasing three-dimensional imaging systems have been constructed according to the foregoing with frame rates of at least ten frames per second, frame rates of at least twenty frames per second, and frame rates between 25 and 30 frames per second.

It will be appreciated that the ability of certain systems, such as multiaperture camera systems, to derive three-dimensional data from two-dimensional video image sets may depend in part on an ability to establish correspondence of surface points between image pairs (or triplets, and so on). The process of establishing point correspondences may be improved by identifying, within the processing system, unique features of the surface upon which correspondence may be based. In certain aspects, distinguishing features of teeth at varying levels of detail may be employed to enhance this process. However, this process depends on an ability to locate such distinguishable features. The process of establishing point correspondences may also, or instead, be enhanced by the addition of optically detectable features thereto, which may be as simple as artificial black dots distributed over a white or relatively light surface. In a dental context, this may be achieved with a spray, powder, mouth rinse, or the like that distributes optically detectable matter across the dentition or other dental object to be scanned. By randomly distributing such small, distinguishable dots across the surface, the likelihood of locating distinguishable features in a particular image set may be significantly improved, thus improving the speed and accuracy of the overall three-dimensional data acquisition process.

From time to time in continuous or incremental data acquisition systems, the fitting or stitch between two frames may fail for reasons described in greater detail below. In such situations, a user may be notified through visual feedback that a recover mode has been entered. In the recover mode, the system 100 may seek to reacquire the previous scan by test fitting new scan data to previously acquired data, and providing visual feedback to a user to assist in navigating back to a scan location on the subject where the re-acquisition is being attempted. In a related landing mode, a user may attempt to initiate a new scan registered or connected to an existing three-dimensional model. Similar visual feedback tools may be provided to guide a user to an appropriate scan location, and notify a user when the scan has been reacquired. These techniques are described in greater detail in commonly-owned U.S. application Ser. No. 11/383,623, filed on May 16, 2006. Other suitable techniques may be employed for navigation, controlling scan quality, analyzing scanned subject matter, and manipulating scanned models, various embodiments of which are described in greater detail below.

The display 110 may include any display suitable for video or other rate rendering at a level of detail corresponding to the acquired data or a rendered version of the acquired data. Suitable displays include cathode ray tube displays, liquid crystal displays, light emitting diode displays, plasma displays, and the like. In some embodiments, the display may include a touch screen interface using, for example capacitive, resistive, or surface acoustic wave (also referred to as dispersive signal) touch screen technologies, or any other suitable technology for sensing physical interaction with the display 110. In addition, where three-dimensional visualization is desired, the display 110 may include a three-dimensional display using a wide variety of techniques including stereo pair imaging, holographic imaging, and multiplanar or volumetric imaging, each with a number of rendering modalities that may be usefully employed with the systems described herein.

Figure 2:
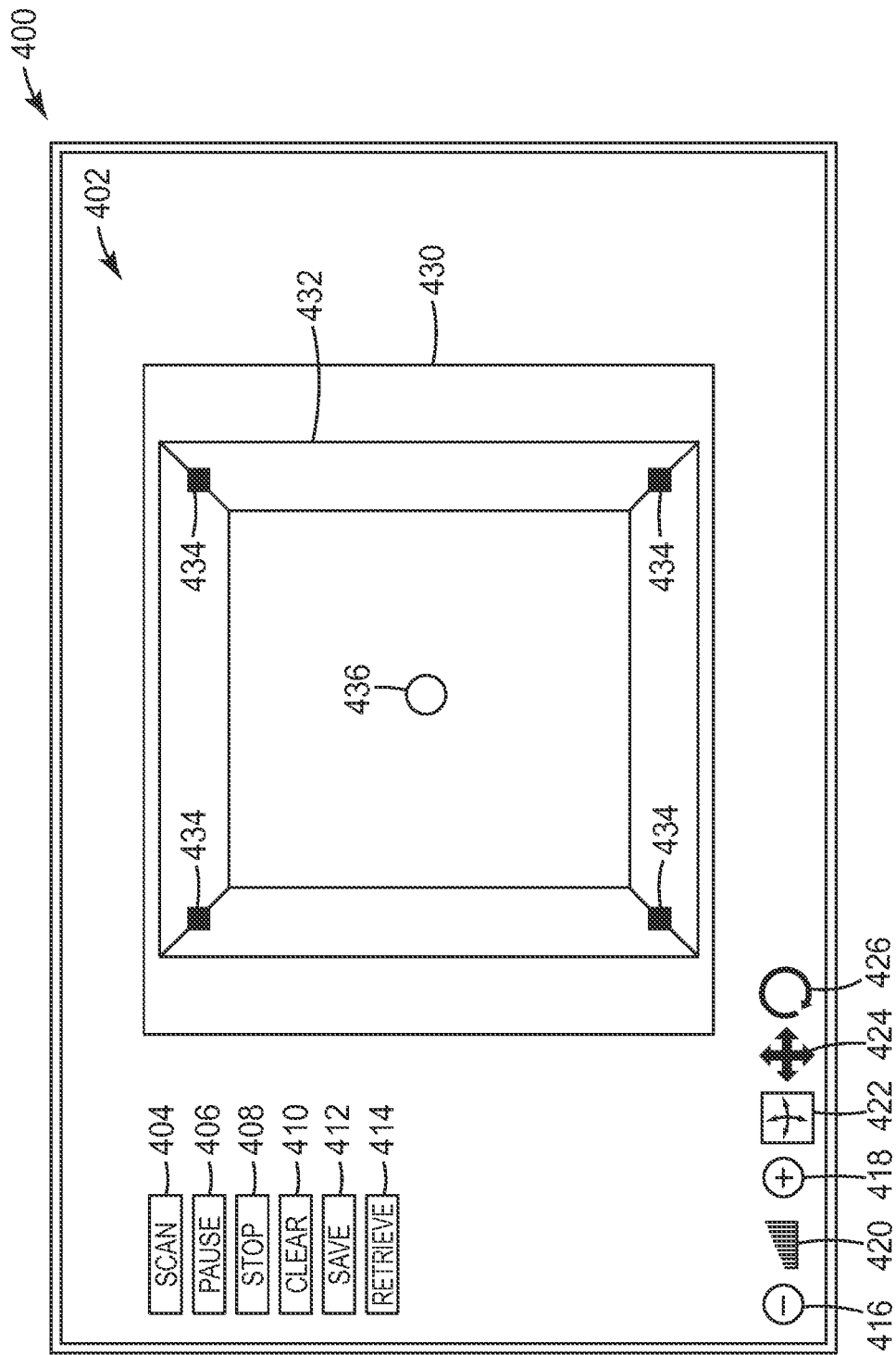
FIG. 2 depicts a view of a user interface for an image capture system.

FIG. 2 depicts a view of a user interface for an image capture system. The user interface 200 may include a window 202 rendered on a monitor such as the display 110 of FIG. 1. Within the window 202, a video image may be displayed including a measurement volume of a scanner, such as the image plane 106 of the scanner 102 of FIG. 1. Within the field of view or measurement volume, a video or other image of a subject such as the subject 104 of FIG. 1 may be displayed. However, as depicted in FIG. 2, no image acquisition steps have been initiated, so the window 202 remains blank except for various controls which will be described below.

Scanning controls may include, for example, a scan control 204, a pause control 206, a stop control 208, a clear control 210, a save control 212, and a retrieve control 214. The scan control 204 may initiate a three-dimensional scan. The pause control 206 may temporarily discontinue a scan in a manner that permits subsequent reacquisition of a continuous scanning process. The paused scan may exhibit a number of visual properties. For example, the video image may be frozen, or the video image may continue to display current video information while a point cloud or other scan data remains frozen, or the screen may go entirely blank, or some combination of these, all according to user preferences or a particular implementation. In general, a paused scan may remain active so that a user may resume the scan. By contrast, if a user activates the stop control 208, the scan may be terminated, such that a user would have to retrieve the scan, such as using the retrieve control 214 in order to continue adding data thereto. The save control 212 may store a scan and any related data for subsequent use. These controls may operate as buttons that a user activates to perform the indicated function, such as through a mouse click or, where the display 110 is a touchscreen, by direct physical interaction with the display 110. It will be appreciated that activation of the control may create a pop-up window, or provide drop down lists, radio buttons, text input fields, and any other controls suitable for parameterizing the particular selection. Thus for example, where a user activates the save control 212, a text box may appear for a user to enter a filename, directory or path information, and the like for saving any related data. Numerous techniques for organizing user interfaces and providing controls within a user interface are known in the art, and may be suitably adapted to the interface 200 described herein.

A number of navigation controls may be provided, such as a zoom out control 216, a zoom in control 218, a zoom indicator 220, a rotate control 222, a pan control 224, and a reset control 226. These controls may be used to view an acquired three-dimensional representation after a scan has been completed or, where a pause/resume feature is provided, during a scan. The reset control 226 may, for example, restore a view of a three-dimensional representation to a global coordinate system, or to a most recent view from which data was acquired during a scan.

A number of range finding visualizations may also be included that provide visual cues related to one or more scanning parameters of an image capture system. These visualizations may be rendered in real time, for example, at the video rate of the image capture system, to provide real time user feedback and guidance with respect to proper orientation and positioning of a scanner during a scan. The user feedback may improve the quality and speed of data acquisition, particularly during continuous scanning operations that acquire a full three-dimensional representation of a subject as a sequence of fitted three-dimensional surface samples. These visual cues may be particularly useful in continuous three-dimensional data acquisition systems based upon camera motion estimation or similar techniques. In such techniques, sequential frames of data are registered to one another using various processing techniques such as those described in commonly owned U.S. application Ser. No. 11/270,135, filed on Nov. 9, 2005. This works well provided three-dimensional data can be successfully resolved from each sequential frame of image data, and there is sufficiently small displacement of the scanner that the data from sequential frames overlaps in three-dimensional space. However, when this "stitching" of sequential frames is lost, such as due to an operator moving outside the proper scanning distance, it can be very difficult to recover the continuous acquisition. Visualization tools that guide a user toward maintaining proper scanning distance advantageously promote a continuous, uninterrupted acquisition of three-dimensional data for an entire surface of interest.

For example, within a window 230 that shows a current video image from the image plane 106 of the scanner 102 (which is blank in FIG. 2, as the system has not started a scan), a volume 232 of space, such as the box depicted in FIG. 2, for which quality scan data can be captured may be depicted in perspective. This volume 232 rendered within the imaging space may assist a user in positioning subject matter within the video image appropriately for data acquisition. In addition, sliders 234 may be animated along z-axis edges of the volume 232 to indicate a distance of points of three-dimensional data actually being acquired. This may be based on, for example, a mean distance of some or all of the points, a distance of a central point, a range of distances for all or some of the points, or a distance of a point at each respective corner of the volume 232, such that the sliders 234 may move independently from one another during a scan. Distance calculations may be based on a current frame of image data, that is, the most recently acquired data set, or an average of a predetermined number of immediately prior data sets, or upon all three-dimensional points of the three-dimensional surface representation falling within the volume 432 without regard to when they were acquired.

As another example, a dynamic object 236 such as a sphere or bullseye may be rendered in the center of the window 230. The dynamic object 236 may also, or instead, be positioned at another location within the window; however positioning the dynamic object 236 within the center of the window 230 advantageously permits a user to receive visual feedback from the dynamic object 236 without looking away from current video of the subject being scanned.

A number of useful animations may be provided by the dynamic object 236 to give user feedback to an operator of the image capture system 100. In one implementation, the dynamic object 236 may be an animated bullseye that is color-coded to provide distance information. The bullseye may, for example be rendered as concentric rings of different colors, such as red, white, and blue, with the central color filling the entire bullseye when a subject is properly distanced from the scanner. When the scanner moves too far from the subject, a red ring may form around the white circle filling a greater portion of the bullseye as the scanner moves further from a subject until the entire bullseye is completely red. Conversely, when the scanner moves too close to a subject, a blue circle may appear within the center of the white circle and grow in size as the scanner moves farther from the subject until the entire circle is blue. In this manner, a user may receive continuous feedback with respect to scan distance—a growing blue central circle as the scanner moves too close, and an engulfing red ring when as the scanner moves too far away—so that the scanner may maintain a proper distance from the subject for continuous acquisition of three-dimensional data in a three-dimensional representation of the subject. One useful model for rendering such a dynamic bullseye employs three co-axial cones of different colors, where the bullseye renders a planar cross-section of the three co-axial cones perpendicular to the common axis, and at a point along the common axis selected according to relative range from the subject.

In another example of animation, three concentric rings may be continuously displayed within the bullseye, with the radius of each ring independently controlled in proportion to the number of points that are too close, properly distanced, and too far. In another possible animation, the center ring (a circle) may move within the bullseye with an offset corresponding to an x-y displacement in the field of view or measurement volume of a region of the surface having the greatest density of points at a target, or desirable, scanning distance.

Of course, it will be appreciated that the selection of colors for such animations is somewhat arbitrary, although significant contrast in hue or intensity may assist a user in recognizing deviations from an optimal scan distance.

Other visual cues and/or metaphors may also, or instead, be employed, such as a visualization of a plane passing through a sphere, active distance bars, animated text, or other visualizations, any of which may provide animated, visual feedback based on, for example, mean distance, center distance, or some other metric that can be derived from scanner output. More generally, visual cues may provide feedback concerning any scanning parameter such as depth of optimal data acquisition, width of field of view, rate of travel or yaw of the scanner 102, density of data acquisition, and so forth, as well as various combinations of these. These visual cues may provide graduated feedback to assist a user in maintaining proper scan distance, and to inform a user when a scan has been lost.

Figure 3:
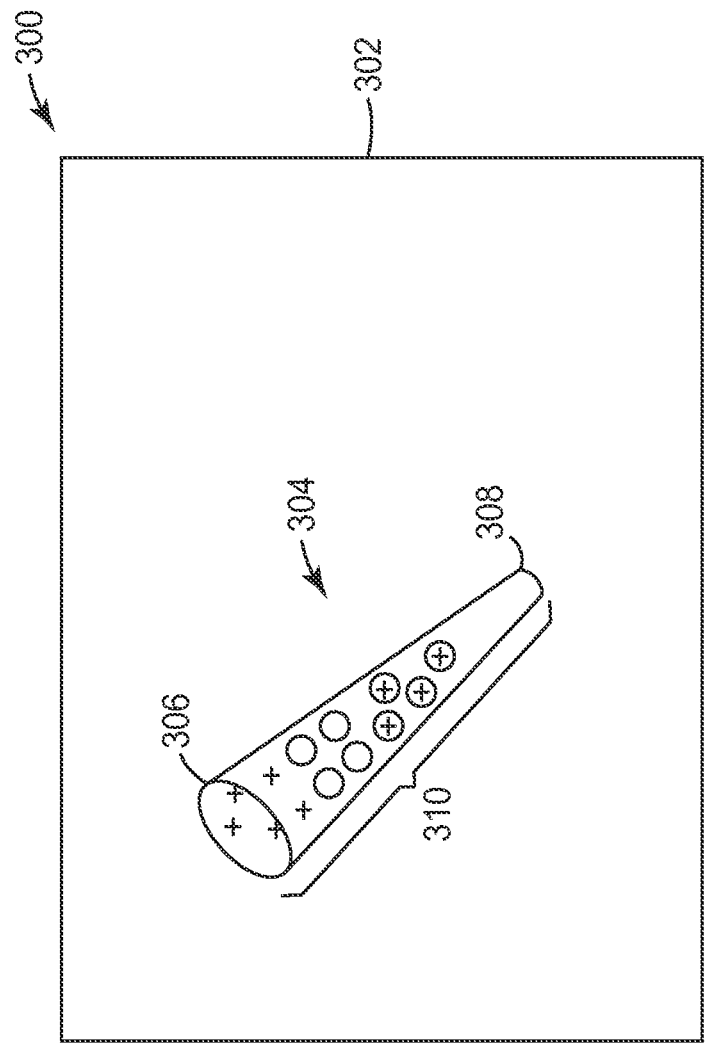
FIG. 3 depicts a view of a user interface for an image capture system.

FIG. 3 depicts a view of a user interface for an image capture system. This abstracted drawing shows a window 302 of the user interface 300, which may be, for example, the window 230 of FIG. 2, without the visual cues described therein. The window 302 may include a video image from a point of view of a scanner such as the image plane 106 of the scanner 102 described above with reference to FIG. 1. Within the window 302, the video image may include a subject 304. As depicted in FIG. 3 (and not by way of limitation), the subject 304 is a slender cylinder extended from a near end 306 relatively close to the scanner to a distant end 308 relatively far from the scanner. During a continuous surface scan of the subject 304, three-dimensional surface data may have been acquired, as indicated generally by x's, o's, and encircled +'s. Within the window 302, the three-dimensional surface scan may be rendered from the point of view of the scanner, along with shading or other visual effects to indicate shape and surface contours. The rendered three-dimensional surface scan may be superimposed in a registered fashion directly over the video image (or conversely, the video image may be superimposed on the rendered three-dimensional surface). This superposition alone provides significant user information, such as what surface regions of the subject 304 have been scanned. In addition, the rendered three-dimensional surface scan may be color-coded or otherwise rendered to provide color information concerning, for example, what region is currently being scanned in the continuous data acquisition process, what regions are too close to acquire scan data from, what regions are at a proper distance for acquisition of surface data, and what regions are too far for surface data. For example, if points on or near the near end 306 of the subject 304 are too close to acquire scan data—these points are indicated in FIG. 3 as x's—they may be rendered in a first color. Points at an optimal scanning distance—indicated in FIG. 3 as o's—may be rendered in a second color. Points too distance for acquisition of three-dimensional data—indicated in FIG. 3 as encircled +'s—may be rendered in a third color. Of course, this distance information may not be directly relevant because the rendered points have already been acquired in three-dimensional space. However, this color coding of the surface of the subject 304, as rendered through the acquired three-dimensional digital surface representation, may provide useful information to a user concerning the distance of the subject 304, particularly with respect to regions of the subject 304 that have not yet been scanned.

It will be appreciated that, while only a dozen or so points have been drawn in FIG. 3, a practical image capture system for use in dentistry and similar applications may require spatial resolution on the order of 100 microns or less for sufficient detail to fabricate properly fitting dental objects. As such, the actual point cloud acquired by the image capture system for a subject such as a dental arch may contain thousands, tens of thousands, hundreds of thousands, or millions of individual three-dimensional points, or more. While the small number of points illustrated in FIG. 3 is intended to assist in explaining the nature of a point cloud distribution and various rendering techniques applicable thereto with reference to the specific points shown (the x's, o's, and encircled x's), the larger number of points available in a typical scan can provide significantly improved visualization of surface contours and the like. It should also be appreciated that the points used to render the digital surface representation for display may include a subset of points in a full point cloud of acquired three-dimensional data, with the density of points selected according to any suitable design parameters including processing/rendering speed, need for contour visualization, and the like. It will also be understood that the data in the three-dimensional scan may be internally represented as points, particle systems, vectors, or any other suitable representation. Thus, while the data may be rendered as a point cloud of any desired density, this may or may not correspond to the internal representation of scan data. Further, the rendering may employ techniques other than point rendering, such as a polygonal mesh or the like, with suitable adaptations to the techniques described above for visualizing range, scan quality, and the like.

It will be appreciated that the capability of capturing highly detailed models of dental objects, and in particular, the capability of capturing highly detailed digital surface representations of dentition directly from an intraoral scan, enables an array of subsequent processing steps that may be useful to dentists, dental laboratory technicians, oral surgeons, and the like. A number of such applications are now described in greater detail.

The embodiments described in reference to FIG. 2 and FIG. 3 emphasize the use of an interface that displays a subject from a point of view of the scanner. However it will be understood that alternative models may be used, such as an interface that renders acquired data from a fixed point of view within a global coordinate system. In an approach employing a fixed point of view, the generally visualization strategy may change, such as by providing continues feedback as to the position of the scanner relative to the subject. However, the visual cues described above may generally be adapted to such an environment, or other environments, in a number of ways as will be readily appreciated by one of skill in the art.

In general, a system as described herein may have a number of operating modes, such as a file management mode, a model editing mode, a model evaluation and/or analysis mode, a scanning mode, and so forth. Two such modes are described with respect to FIGS. 4 and 5 below, which show a scanning mode and an evaluation mode respectively.

Figure 4:
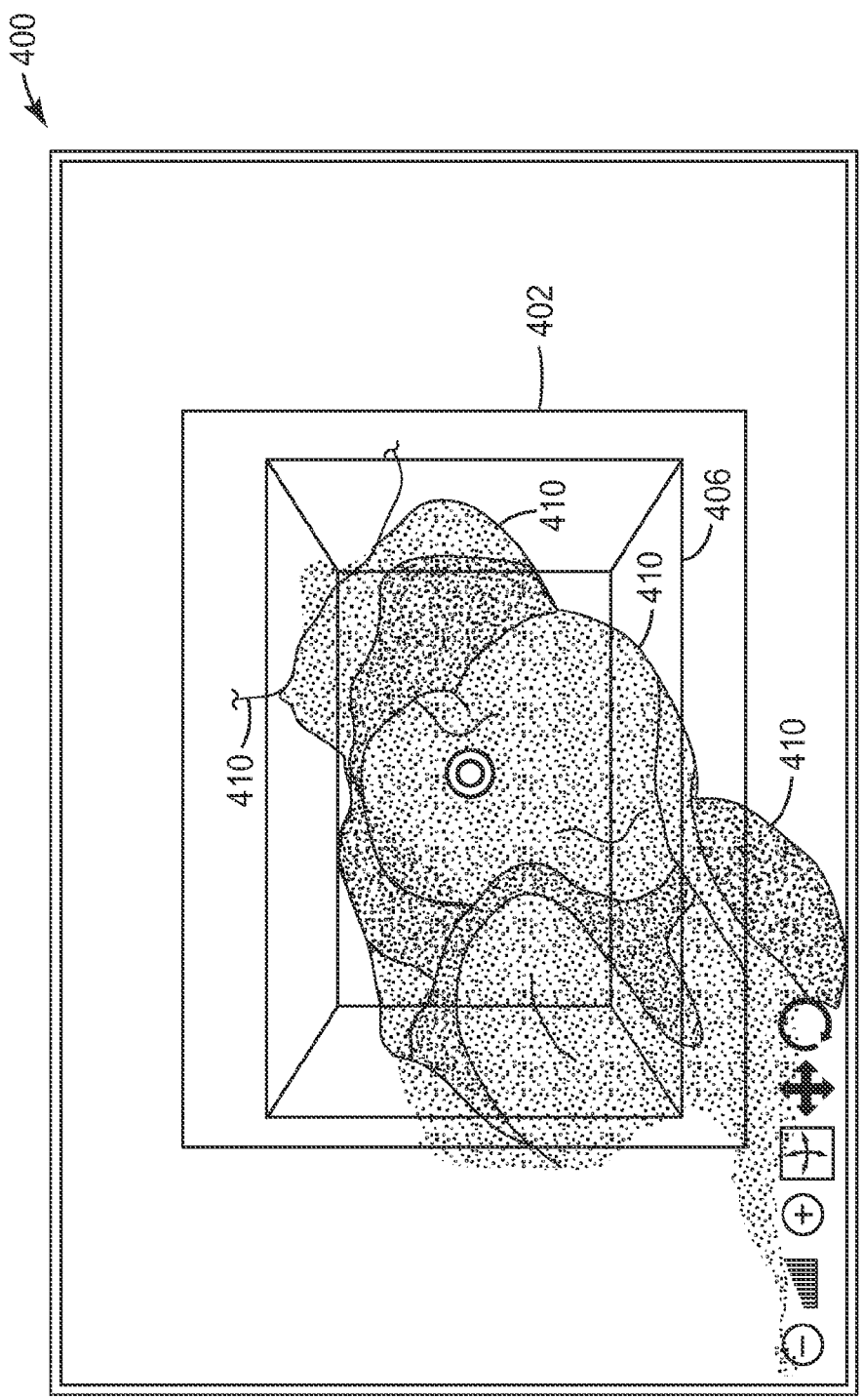
FIG. 4 depicts a view of a user interface for an image capture system during an acquisition of three-dimensional data.

FIG. 4 depicts a view of a user interface for an image capture system during an acquisition of three-dimensional data. The user interface 400 may include a window 402 including range-finding visual cues 404, 406, all as generally described above. Within the window 402, a video image may be displayed, such as a video image from a current point of view of a scanner, such as the scanner 102 described above. As depicted, the video image may include a plurality of teeth 410 and other intraoral structures visible during an intraoral scan. It will be noted that three-dimensional points acquired from the surface, that is, the current digital surface representation, may be rendered within the user interface 400, and more particularly, may be rendered from the point of view of the scanner and superimposed on the current video image.

Although not depicted, it will be understood that in other embodiments, the current digital surface representation may be rendered from a fixed point of view.

In addition to permitting visual enhancements such as contour shading and feature emphasis, the rendering may provide specific feedback to a user concerning the current scan. For example, regions too close for capture of scan data may include previously acquired points, which may be rendered in the window 402 with a style or color that indicates their relative proximity to the scanner. Conversely, regions of the intraoral structures too far for capture may also, or instead, include previously acquired points, which may be rendered in the window 402 with a style or a color that indicates their relative distance from the scanner. As new surface data is acquired and added to the digital surface representation, the new point data may concurrently, or in real time or near real time, be added to the rendered view of the digital surface representation. In this manner, a user may receive immediate visual feedback, such as the density of rendered points or relative fineness/coarseness of a polygonal mesh, with respect to whether data is being successful acquired from surfaces visible within the window 402. This information may indicate gaps in surface data so that a user can back up and rescan surfaces of the subject for which data has not been captured, or for which inadequate or defective data has been captured. This feedback may in part flow directly from the process of rendering an increasing number of points within the window as new surface data is acquired. The visual feedback may also, or instead, be supplemented by rendering points with a density in the window 402 specifically selected to communicate to a user whether adequate data has been acquired from within the current view. While specific feedback examples are noted above, it will be understood that more generally, numerous and various uses of brightness, texture, shading, color, and/or rendered point cloud density, or the like may be employed to provide visual feedback to a user concerning scan quality, detail, and the like.

The visual metaphor may be one of spray painting the video image with a shaded surface map as points are acquired. The point cloud of the digital surface representation (or other representation) may be rendered as a growing constellation of points that forms over the video subject matter as data is acquired. Regions for which a target point density has been achieved may, for example appear as continuous surfaces, while regions with inadequate surface data may be rendered as discrete points having visible gaps therebetween, which gaps may be varied in size according to, for example, the density of point data in the underlying digital surface representation. As another example, points may be rendered as uniformly spaced surface points, which may be color coded according to density of point data in the underlying digital surface representation.

In certain embodiments, the acquired digital model may be compared to a statistical, spatial, or other model of expected shapes relevant to dentistry (or other objects, for non-dental applications), using know machine vision and other techniques. This may include relatively subtle variations such as unexpected tooth contours, thicknesses, or the like, as well as gross deviations that are likely a result of user or equipment malfunction or loss of scan data. Where deviations from expectations are detected, these may be visually identified within the window 402 through use of color, shading, and other cues and annotations described generally above. Thus, algorithmically unexpected scan results may be immediately flagged during a scan for any suitable human intervention (which may, of course, be none where the unexpected feature is known by the operator to actually be present).

Having discussed various aspects of a three-dimensional scanning system, the description now turns to use of space carving to improve processing and display of three-dimensional data.

Figure 5:
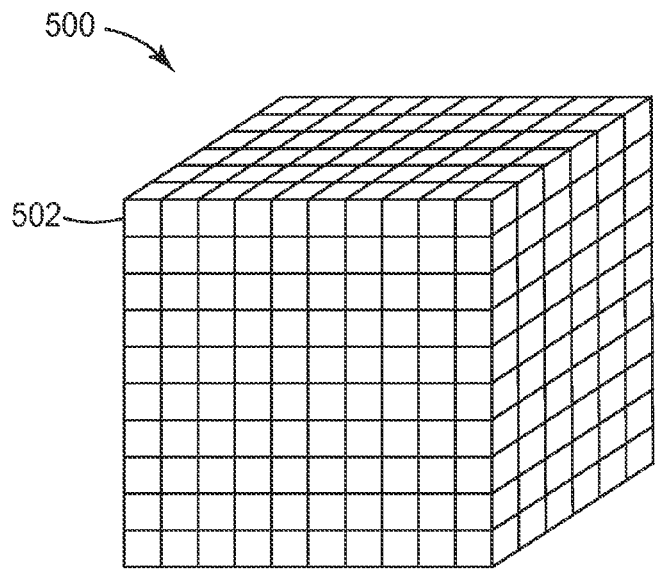
FIG. 5 illustrates a spatial matrix for use in space carving.

FIG. 5 illustrates a spatial matrix for use in space carving. In general, the spatial matrix 500 may include a number of cells 502, each storing information related to a voxel in a scan volume. In one aspect, each cell 502 may store a binary flag that indicates whether the corresponding voxel is permitted or forbidden for processing. This approach advantageously provides a compact memory representation of carved space, however it will be readily appreciated that other representations of this information may also or instead be employed, and that additional information may be included in the spatial matrix such as any information that might be usefully stored on a voxel-by-voxel basis for the volume in which an object is being scanned. It will also be appreciated that, while the spatial matrix 500 is depicted as a three-dimensional structure that maps to the volume of a scan space, no such physical structure is required.

The spatial matrix 500 may include any memory or combination of memories capable of storing and retrieving information according to voxels within the scan space, and all such variations that would be apparent to one of ordinary skill in the art are intended to fall within the scope of this invention. The spatial matrix 500 may define a mesh of voxels that together form the scan volume or scan space in which data is processed as generally described below. In this respect, it will be readily appreciated that while the spatial matrix 500 depicted in FIG. 5 corresponds to a cubic volume, any shape or size of volume may be suitably employed according to the shape and/or size of an object that is being scanned, a processing mesh used for three-dimensional reconstruction, or any other factors. Thus in one aspect, the mesh of the scan space is subdivided into voxels having a substantially cubic shape. The substantially cubic shape may measure about 250 microns on each edge (that is, a 250×250×250 micron cube for each voxel) or any other suitable size according to desired resolution, processing capabilities, and so forth. In one aspect, the spatial matrix 500 may include a binary flag for each one of the plurality of voxels that indicates whether processing is permitted (for example, unmodified) or forbidden (for example, modified) for a volume of the scan space.

Figure 6:
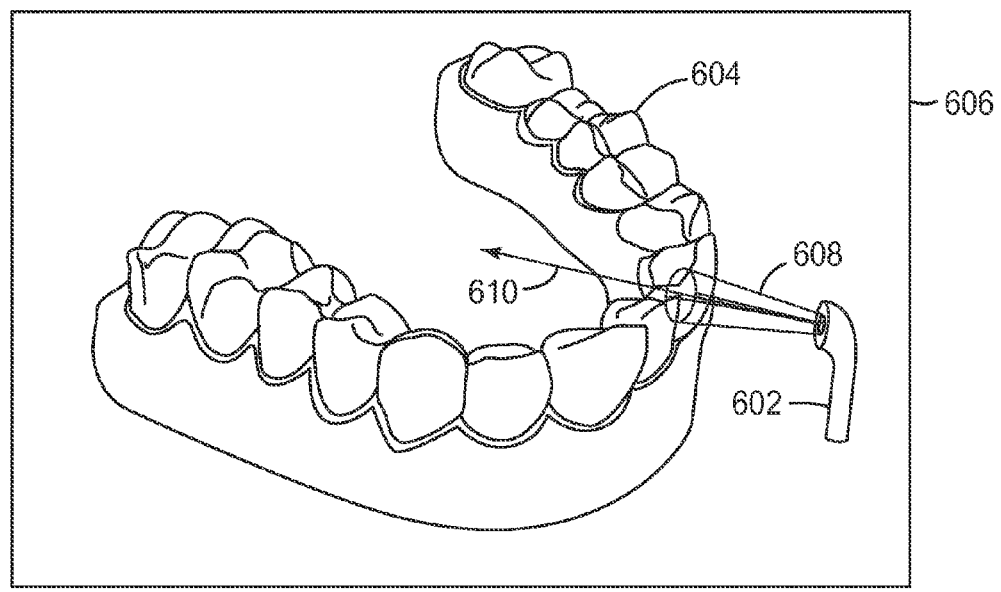
FIG. 6 illustrates a ray trace used to identify unoccupied space.

FIG. 6 illustrates a ray trace used to identify unoccupied space. During a scan such as any of the scans described above, a scanner 602 such as any of the scanners described above may be passed over an object 604 within a scan space 606 to acquire three-dimensional data. While depicted two-dimensionally, it will be understood that the scan space 606 would generally be a three-dimensional volume. Given a position of the scanner 602 and the object 604, one or more rays—straight lines passing through the scan space 606—may be determined such as a first ray 608 that intersects a surface of the object 604 and a second ray 610 that does not intersect a surface of the object 604. With the scan space 606 divided into a volumetric mesh according to the spatial matrix described above, all of the voxels that each ray 608, 610 passes through can be determined, and more particularly, each unoccupied one of the voxels in the mesh can be identified. Each unoccupied one of the voxels may be flagged in the spatial matrix as prohibited using, for example, a binary flag or any other suitable identifier. In this manner, voxels that are known to be unoccupied at some time during the scan can be marked for modified processing and differentially processed during a scan, all as generally contemplated below.

It will be appreciated that numerous variations are possible. For example, a margin around the surface of the object may be provided in which voxels cannot be flagged for differential processing. This may be based on distance from the surface, or on a number of surrounding voxels that are marked for differential processing, or on the actual number of points of three-dimensional data acquired within a voxel of the mesh, and so forth, as well as combinations of the foregoing. In another aspect, a threshold may be provided for a minimum number of rays passing through a voxel before it can be marked for modified processing. Space carving is generally known in the art as a technique for identifying unoccupied volume, and any corresponding techniques or tools may be adapted to identify 'prohibited' voxels as contemplated herein. For example, commercially available software tools such as Voxel Space (Novalogic) and/or 3D-DDA support ray tracing through voxel spaces and may be used with space carving as described herein. As such, algorithms and software tools for space carving are not discussed here in detail, with emphasis being on use of space carving techniques to support differential processing of three-dimensional data.

Figure 7:
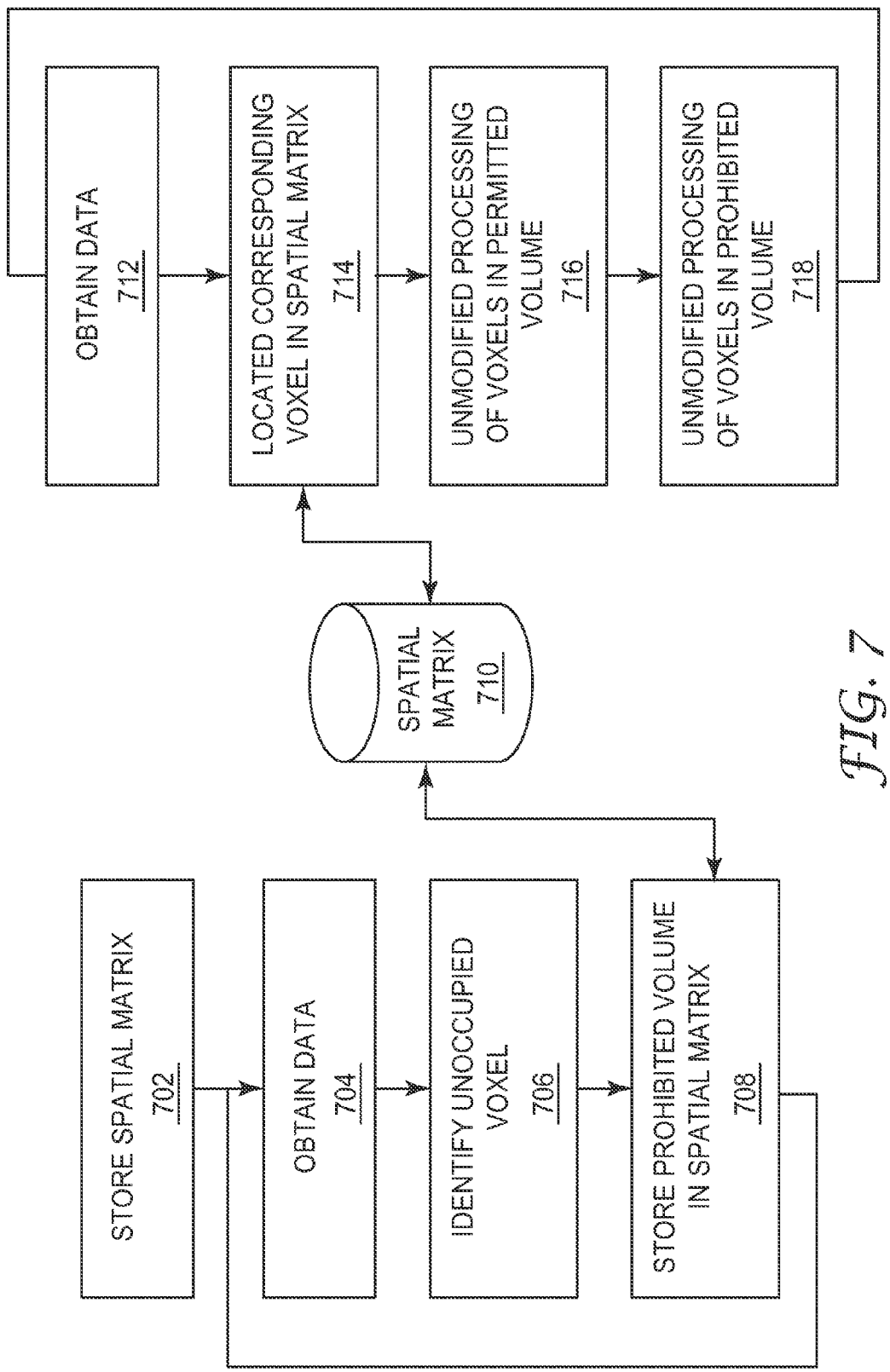
FIG. 7 is a flow chart of a process for displaying data based on a spatial matrix.

FIG. 7 is a flow chart of a process for displaying data based on a spatial matrix. As generally described below, a spatial matrix such as the matrix described above with reference to FIG. 5 may be used to store information about what type of processing is permitted or forbidden for data within voxels of the scan space. While the 'forbidden' voxels may be generally understood as voxels that are unoccupied, it will be appreciated that this is not universally true and that voxels in which points are detected may be forbidden (such as where a surface temporarily moves into a scan space) and voxels that are empty may be permitted (such as where a voxel is immediately adjacent to an occupied voxel. Thus while terms such as occupied or unoccupied are used in this description, these terms should not be understood as a direct proxy for whether data points are or can be obtained from a voxel, or whether a voxel is permitted (that is, receiving unmodified processing) or forbidden (that is, receiving modified processing).

As shown in step 702, the process 700 may begin with storing a spatial matrix in a memory, such as the spatial matrix described above that includes information for a plurality of voxels in a mesh of a scan space.

As shown in step 704, three-dimensional data may be obtained from an object within a scan space using, for example, any of the scanners described above.

As shown in step 706, the process 700 may include identifying at least one of the plurality of voxels in the scan space that is unoccupied. This may be accomplished, for example, using any suitable ray tracing software or algorithm. A variety of commercially available software tools (for example 3D-DDA) and general algorithms (for example, Bresenham's line algorithm) are known in the art for traversing voxels in a space and identifying what voxels contain a ray, any of which may be usefully adapted to identifying unoccupied voxels in a scan space as contemplated herein. In a ray tracing embodiment, unoccupied space may, for example, include voxels behind or beyond a known surface of an object, or voxels between a scanner and the surface, as well as combinations of these. In another aspect, other information may also or instead be used to determine whether a voxel should be forbidden or permitted. For example, for a voxel to be forbidden, the process 700 may provide a threshold for a minimum number of adjacent voxels that are already identified as forbidden. In another aspect, the number of rays passing through a voxel may be counted and used, for example, as a minimum threshold for identifying a voxel as forbidden. For occluded surfaces of the scanned object, the process 700 may provide an offset or step away from the border of the occlusion in a field of view. More generally, any suitable techniques for characterizing a voxel as containing or not containing the surface of interest may be suitably employed to identify prohibited space as contemplated herein.

In one aspect, voxels in a spatial margin of one or more voxels adjacent to a surface of an object being scanned may be prevented from being flagged as prohibited. That is, in order to ensure accuracy of the model, immediately adjacent data may be included regardless of whether an associated voxel is believed to be unoccupied. The spatial margin may, for example, be a single layer of voxels, or a number or depth of voxels as determined, for example, with reference to a standard deviation of z-axis measurements of a scanner. Thus for example, a voxel may be treated as 'permitted' regardless of whether it is occupied by three-dimensional data points if the voxel is within a distance from the surface of a scan subject that is less than one standard deviation, two standard deviations, or some other multiple of the standard deviation of z-axis measurements of the scanner. By controlling this metric, a scanning process may include more or less marginal data that is adjacent to but not on an inferred surface of the object.

As shown in step 708, the process 700 may include storing an indication for modified processing of the one of the plurality of voxels in the spatial matrix 710. After completing this step for one or more of the plurality of voxels, the spatial matrix identifies a prohibited volume that includes one or more voxels within the scan space. It will be understood that identifying the prohibited volume may be a cumulative process that is repeated as each new frame of three-dimensional data is repeated for a scan such as the sequential scans described above. Thus for example, each frame of data may provide different information on surfaces of the object that are occluded, that have changed, or that have disappeared, and this information may be generally used to update the spatial matrix in any suitable way. In general, it is contemplated that every voxel of the matrix is a permitted voxel until a reliable inference can be made that the voxel should be prohibited. However, this is not strictly required, and variations to this initial condition may be made without departing from the scope of this disclosure.

As noted above, a voxel in the prohibited volume—that is, a voxel that receives modified processing—is not necessarily a voxel that is unoccupied. For example, if a new frame of data provides a first instance of a point, surface, or object that is not in a voxel in previous frames of data, then the voxel is occupied even though nominally 'prohibited'. Conversely, an unoccupied voxel may be nominally 'permitted,' such as a margin of voxels around a surface of an object, or a voxel for which sufficient data has not yet been acquired to conclude that the voxel should receive modified processing (that is, that the voxel is 'prohibited'). The prohibited volume may generally include more than one of the voxels in the mesh or spatial matrix.

The process 700 may then return to step 704 where additional three-dimensional data is obtained.

Concurrently with or subsequent to the identification of a prohibited volume, the process 700 may engage in a three-dimensional scanning process to obtain a three-dimensional surface representation or other digital model of a scan subject.

As shown in step 712, the process 700 may include obtaining three-dimensional data. This may be the same data acquired in step 704, or different data, or some combination of these.

As shown in step 714, one or more corresponding voxels may be identified in the spatial matrix 710. In this step, the location may be used to retrieve a processing indicator such as a 'permitted' or 'forbidden' flag for voxels from the spatial matrix 710. This information may in turn be used to apply differential processing as described below.

As shown in step 716, the process 700 may include processing a portion of the three-dimensional data that is not in the prohibited volume—or alternatively stated, three-dimensional data that is in the permitted volume of the scan space—according to an unmodified or normal processing. This may include any processing associated with the acquisition of three-dimensional data such as derivation of a camera path for a scanner, feature-based or other derivation of individual three-dimensional data points from frames of video or image data, registration of three-dimensional surfaces and so forth. In general, it is contemplated that any three-dimensional process that does not use space carving or the like may be performed in an 'unmodified' processing step as that term is used herein, including without limitation acquisition, display, and refinement (for example, optimization, error minimization, etc.) of a three-dimensional surface representation based on, for example, a sequence of frames of image data or the like from a three-dimensional scanner.

As shown in step 718, the process 700 may include processing a portion of the three-dimensional data that is in the prohibited volume according to the modified processing. Modified processing may include any processing suitable for data in the 'prohibited' volume.

Modified processing may, for example, include selective use of three-dimensional data points in a three-dimensional reconstruction according to whether they are in prohibited or permitted volumes of the scan space. For example, a reconstruction process may treat data within the prohibited volume as outliers that are excluded from processing. Or data in the prohibited volume may be de-weighted or otherwise de-emphasized in the reconstruction process. This data exclusion or de-weighting may be performed in a real time reconstruction process while three-dimensional data is being displayed, or in a post-processing refinement step, or some combination of these. Thus in one aspect, modified processing includes omitting any points in the prohibited volume from a high-accuracy refinement of the three-dimensional data.

In another aspect, modified processing may include controlling how data in the prohibited volume is displayed. For example, data within the prohibited volume may be excluded from display, or may be displayed temporarily using a brief decay time such as 0.5 seconds or any other short interval.

In another aspect, modified processing may include controlling how data in the prohibited volume is used in a surface mesh of the three-dimensional data. For example, points in the prohibited volume may be excluded from a surface mesh of the scanned object created from the three-dimensional (point) data using a marching cubes grid or other surface mesh algorithm. In another aspect, where a processing grid for the surface mesh is identical (or substantially identical) to the mesh of the spatial matrix, voxels from the prohibited volume may be excluded entirely from the surface mesh. Surface mesh generation is a known technique for representing a three-dimensional shape as a collection of vertices, edges and faces that form polygons (for example, triangles, quadrilaterals). In one aspect, the processing mesh for generating such a surface from the three-dimensional data may be co-extensive and equally dimensioned with the mesh used for the spatial matrix, although this is not strictly required. Thus in one aspect the mesh of the scan space used for the spatial matrix may divide the scan space into a spatial grid that is substantially identical to a second spatial grid used to create a surface mesh from the three-dimensional data. In another aspect, the meshes may provide different processing resolutions and/or be unaligned spatially.

After modified and/or unmodified processing has been performed on three-dimensional data, the process 700 may return to step 712 where additional three-dimensional data is acquired. This process 700 may continue until a scan is manually or automatically stopped, or otherwise terminated.

As such there is generally disclosed herein methods and systems for differential processing of data in a three-dimensional data acquisition process according to where the data occurs in a scan space. It will be appreciated that, while the process 700 of FIG. 7 is representative, numerous variations may be made without departing from the scope of the invention. For example space carving and data processing (for example, of steps 716, 718) may be performed independently, or within a single repeating sequential process, or some combination of these. In addition, identifying the prohibited volume, or portions thereof, may be performed before, during, or after the data processing of steps 716 and 718, or some combination of these. Still more generally, any order and combination of steps that might be recognized as useful for identifying forbidden/permitted voxels in a scan space on one hand, and acquiring data for a three-dimensional reconstruction on the other, may be adapted to use with the methods and systems described herein without departing from the scope of this disclosure.

It will be appreciated that the processes and methods disclosed above may be realized in hardware, software, or any combination of these suitable for the three-dimensional imaging and modeling techniques described herein. It will also be appreciated that the user interfaces, user interface controls, and methods of using same, as well as the visualizations, digital model processing and analysis, and rendering as described herein may similarly be expressed as methods or processes embodied in hardware, software, and various combinations thereof. Thus in one aspect there is disclosed herein a computer program product comprising computer executable code stored in a transitory or non-transitory medium that, when executing on one or more computers, performs any one or more of the steps described above.

This also includes realization in one or more microprocessors, microcontrollers, embedded microcontrollers, programmable digital signal processors or other programmable devices, along with internal and/or external memory. The hardware may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer in a number of ways or all of the functionality may be integrated into a dedicated, standalone image capture device. All such permutations and combinations are intended to fall within the scope of the present disclosure.

It will also be appreciated that means for performing the steps associated with the processes described above may include any suitable components of the image capture system 100 described above with reference to FIG. 1, along with any software and/or hardware suitable for controlling operation of same. The user interfaces described herein may, for example, be rendered within the display 110 of the image capture system 100 of FIG. 1. All such realizations and means for performing the processes disclosed herein are intended to fall within the scope of this disclosure.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method comprising:
    storing a spatial matrix in a memory, the spatial matrix including information for a plurality of voxels in a mesh of a scan space;
    obtaining three-dimensional data from an object within the scan space using a scanner;
    identifying a one of the plurality of voxels in the mesh that is unoccupied;
    storing an indication in the spatial matrix for a modified processing of data from the one of the plurality of voxels, thereby identifying a prohibited volume within the scan space; and
    processing a portion of the three-dimensional data that is not in the prohibited volume according to an unmodified processing and processing a second portion of the three-dimensional data that is in the prohibited volume according to the modified processing, wherein the modified processing includes detecting a point in the prohibited volume and displaying the point for a decay time with the second portion of the three-dimensional data.

2. The method of claim 1 wherein identifying the one of the plurality of voxels includes identifying a plurality of points on a ray between the scanner and the object that are unoccupied.

3. The method of claim 1 further comprising providing a spatial margin of one or more voxels adjacent to a surface of the object for which processing cannot be prohibited.

4. The method of claim 3 wherein the spatial margin is a multiple of a standard deviation of a z-axis measurement for the scanner.

5. The method of claim 1 wherein the modified processing includes omitting any points in the prohibited volume from a surface mesh of the object created with the three-dimensional data.

6. The method of claim 5 wherein the mesh divides the scan space into a spatial grid substantially identical to a second spatial grid used to create the surface mesh.

7. The method of claim 1 wherein the modified processing includes omitting any points in the prohibited volume from a high-accuracy refinement of the three-dimensional data.

8. The method of claim 1 wherein the mesh of the scan space is subdivided into voxels having a substantially cubic shape.

9. The method of claim 8 wherein the substantially cubic shape measures about 250 microns on each edge.

10. The method of claim 1 wherein the prohibited volume includes more than one of the plurality of voxels.

11. The method of claim 1 wherein the spatial matrix includes a binary flag for each one of the plurality of voxels that indicates whether processing is permitted or forbidden for a corresponding volume of the scan space.

12. A computer program product comprising computer executable code embodied on a non-transitory computer readable medium that, when executing on one or more computing devices, performs the steps of:
    storing a spatial matrix in a memory, the spatial matrix storing information for a plurality of voxels in a mesh of a scan space;
    obtaining three-dimensional data from an object within the scan space using a scanner;
    identifying one of the plurality of voxels in the mesh of the scan space that is unoccupied;
    storing an indication in the spatial matrix for a modified processing of data from the one of the plurality of voxels, thereby identifying a prohibited volume within the scan space; and
    processing a portion of the three-dimensional data in the prohibited volume according to the modified processing and processing a second portion of the three-dimensional data that is not in the prohibited volume according to an unmodified processing, wherein the modified processing includes detecting a point in the prohibited volume and displaying the point for a decay time with the second portion of the three-dimensional data.

13. The computer program product of claim 12 wherein identifying the one of the plurality of voxels includes identifying a plurality of points on a ray between the scanner and the object that are unoccupied.

14. The computer program product of claim 12 further comprising code for providing a spatial margin of one or more voxels adjacent to a surface of the object for which processing cannot be prohibited.

15. The computer program product of claim 14 wherein the spatial margin is a multiple of a standard deviation of a z-axis measurement for the scanner.

16. The computer program product of claim 12 wherein the modified processing includes omitting any points in the prohibited volume from a surface mesh of the object created with the three-dimensional data.

17. The computer program product of claim 16 wherein the mesh divides the scan space into a spatial grid substantially identical to a second spatial grid used to create the surface mesh.

18. The computer program product of claim 12 wherein the modified processing includes omitting any points in the prohibited volume from a high-accuracy refinement of the three-dimensional data.

19. The computer program product of claim 12 wherein the mesh of the scan space is subdivided into voxels having a substantially cubic shape.

20. The computer program product of claim 19 wherein the substantially cubic shape measures about 250 microns on each edge.

21. The computer program product of claim 12 wherein the prohibited volume includes more than one of the plurality of voxels.

22. The computer program product of claim 12 wherein the spatial matrix includes a binary flag for each one of the plurality of voxels that indicates whether processing is permitted or forbidden for a corresponding volume of the scan space.

23. A system comprising:
    a scanner configured to obtain three-dimensional data from an object within a scan space;
    a memory configured to store a spatial matrix that includes information for a plurality of voxels in a mesh of the scan space; and
    a processor configured to identify a point in the scan space that is unoccupied, to store an indication in the spatial matrix for a modified processing of data from a one of the plurality of voxels that contains the point, thereby identifying a prohibited volume within the scan space, to process a portion of the three-dimensional data that is not in the prohibited volume according to an unmodified processing, and to process a second portion of the three-dimensional data that is in the prohibited volume according to the modified processing, wherein the modified processing includes detecting a point in the prohibited volume and displaying the point for a decay time with the second portion of the three-dimensional data.

24. A computer program product comprising computer executable code embodied on a non-transitory computer readable medium that, when executing on one or more computing devices, performs the steps of:

storing a spatial matrix in a memory, the spatial matrix storing information for a plurality of voxels in a mesh of a scan space;

obtaining three-dimensional data from an object within the scan space using a scanner;

providing a spatial margin of one or more voxels adjacent to a surface of the object for which processing cannot be prohibited, wherein the spatial margin is a multiple of a standard deviation of a z-axis measurement for the scanner;

identifying one of the plurality of voxels in the mesh of the scan space that is unoccupied;

storing an indication in the spatial matrix for a modified processing of data from the one of the plurality of voxels, thereby identifying a prohibited volume within the scan space; and processing a portion of the three-dimensional data in the prohibited volume according to the modified processing and processing a second portion of the three-dimensional data that is not in the prohibited volume according to an unmodified processing.

25. The computer program product of claim 24 wherein the modified processing includes omitting any points in the prohibited volume from a surface mesh of the object created with the three-dimensional data.

26. The computer program product of claim 25 wherein the mesh divides the scan space into a spatial grid substantially identical to a second spatial grid used to create the surface mesh.

* * * * *